US007975733B2

(12) United States Patent
Horppu et al.

(10) Patent No.: US 7,975,733 B2
(45) Date of Patent: Jul. 12, 2011

(54) FLUID TRANSFER DEVICE

(75) Inventors: Petri Horppu, Göteborg (SE); Anna Ellström, Mölndal (SE)

(73) Assignee: Carmel Pharma AB, Göteborg (SE)

( * ) Notice: Subject to any disclaimer, the term of this patent is extended or adjusted under 35 U.S.C. 154(b) by 927 days.

(21) Appl. No.: 11/745,702

(22) Filed: May 8, 2007

(65) Prior Publication Data

US 2008/0277021 A1 Nov. 13, 2008

(51) Int. Cl.
*A61M 5/32* (2006.01)

(52) U.S. Cl. .......... 141/330; 141/22; 141/379; 141/384; 604/414

(58) Field of Classification Search .................... 141/18, 141/21–22, 329–330, 379, 384; 604/411, 604/414
See application file for complete search history.

(56) References Cited

U.S. PATENT DOCUMENTS

| | | | | |
|---|---|---|---|---|
| 1,844,342 | A | 2/1932 | Berman | |
| 2,010,417 | A | 8/1935 | Schwab | |
| 2,697,438 | A | 12/1954 | Hickey | |
| 2,717,599 | A | 9/1955 | Huber | |
| 3,064,651 | A | 11/1962 | Henderson | |
| 3,071,135 | A | 1/1963 | Baldwin et al. | |
| 3,308,822 | A | 3/1967 | DeLuca | |
| 3,316,908 | A | 5/1967 | Burke | |
| 3,340,671 | A | 9/1967 | Loo | |
| 3,390,677 | A * | 7/1968 | Razimbaud | 604/414 |
| 3,448,740 | A | 6/1969 | Figge | |
| 3,542,240 | A | 11/1970 | Solowey | |
| 3,783,895 | A | 1/1974 | Weichselbaum | |
| 3,788,320 | A | 1/1974 | Dye | |
| 3,822,700 | A | 7/1974 | Pennington | |
| 3,938,520 | A | 2/1976 | Scislowicz et al. | |
| 3,976,073 | A | 8/1976 | Quick et al. | |
| 4,096,860 | A | 6/1978 | McLaughlin | |
| 4,296,786 | A | 10/1981 | Brignola | |
| D270,568 | S | 9/1983 | Armstrong | |
| 4,490,139 | A | 12/1984 | Huizenga et al. | |
| 4,516,967 | A | 5/1985 | Kopfer | |

(Continued)

FOREIGN PATENT DOCUMENTS

| | | |
|---|---|---|
| AU | 200112863 | 5/2003 |

(Continued)

OTHER PUBLICATIONS

Taiwan Search Report for Taiwan Patent Application 092106323 dated Mar. 21, 2003 (4 pages).

(Continued)

*Primary Examiner* — Gregory L Huson
*Assistant Examiner* — Nicolas A Arnett
(74) *Attorney, Agent, or Firm* — Fish & Richardson P.C.

(57) ABSTRACT

A fluid transfer device for transferring fluid from a first fluid container to a second fluid container such as a piercing member protection device is provided. The fluid transfer device can include a longitudinal axis and a first connection part having a connection means for connecting to a first fluid container. The fluid transfer device can further include a second connection part rotatably mounted to the first connection part by mounting means, and the second connection part can further include connection means for connecting a second fluid container. The mounting means can enable turning of the second connection part with respect to the first connection part. Such a device can allow a user to safely turn e.g., a syringe after assembly to read a volume indication or similar.

25 Claims, 3 Drawing Sheets

U.S. PATENT DOCUMENTS 4,564,054 A * 1/1986 Gustavsson .................. 141/329
4,573,967 A 3/1986 Hargrove et al.
4,576,211 A * 3/1986 Valentini et al. .............. 141/329
4,581,016 A 4/1986 Gettig
4,582,223 A 4/1986 Kobe
4,588,403 A 5/1986 Weiss et al.
4,600,040 A 7/1986 Naslund
4,623,343 A 11/1986 Thompson
4,629,455 A 12/1986 Kanno
4,632,673 A 12/1986 Tiitola et al.
4,636,204 A 1/1987 Christopherson et al.
4,673,400 A 6/1987 Martin
4,673,404 A 6/1987 Gustavsson
4,737,150 A 4/1988 Baeumle et al.
4,752,287 A 6/1988 Kurtz et al.
4,759,756 A 7/1988 Forman et al.
4,768,568 A 9/1988 Fournier et al.
4,792,329 A 12/1988 Schreuder
4,804,015 A 2/1989 Albinsson
4,822,340 A 4/1989 Kamstra
4,826,492 A 5/1989 Magasi
4,834,717 A 5/1989 Haber et al.
4,842,585 A 6/1989 Witt
4,850,978 A 7/1989 Dudar et al.
4,864,717 A 9/1989 Baus, Jr.
4,872,494 A * 10/1989 Coccia .......................... 141/329
4,878,897 A 11/1989 Katzin
4,889,529 A 12/1989 Haindl
4,898,209 A 2/1990 Zbed
4,909,290 A 3/1990 Coccia
4,932,937 A 6/1990 Gustavsson et al.
4,944,736 A 7/1990 Holtz
4,964,855 A 10/1990 Todd et al.
4,982,769 A 1/1991 Fournier et al.
4,994,048 A 2/1991 Metzger
4,997,083 A 3/1991 Loretti et al.
5,017,186 A 5/1991 Arnold
5,041,105 A 8/1991 D'Alo et al.
5,061,264 A 10/1991 Scarrow
5,071,413 A 12/1991 Utterberg
5,122,116 A 6/1992 Kriesel et al.
5,122,123 A 6/1992 Vaillancourt
5,137,524 A 8/1992 Lynn et al.
5,158,554 A 10/1992 Jepson et al.
5,176,673 A 1/1993 Marrucchi
5,199,947 A 4/1993 Lopez et al.
5,201,725 A 4/1993 Kling
5,207,658 A 5/1993 Rosen et al.
5,232,109 A 8/1993 Tirrell et al.
5,254,097 A 10/1993 Schock et al.
5,279,576 A 1/1994 Loo et al.
5,279,583 A * 1/1994 Shober et al. ................. 604/414
5,279,605 A 1/1994 Karrasch et al.
5,308,347 A 5/1994 Sunago et al.
5,312,366 A 5/1994 Vaillancourt
5,328,480 A 7/1994 Melker et al.
5,334,163 A 8/1994 Sinnett
5,356,406 A 10/1994 Schraga
5,385,545 A 1/1995 Kriesel et al.
5,385,547 A 1/1995 Wong et al.
5,389,085 A 2/1995 D'Alessio et al.
5,405,326 A 4/1995 Haber et al.
5,445,630 A 8/1995 Richmond
5,447,501 A 9/1995 Karlsson et al.
5,456,675 A 10/1995 Wolbring et al.
5,470,522 A 11/1995 Thome et al.
5,478,328 A 12/1995 Silverman et al.
5,478,337 A 12/1995 Okamoto et al.
5,492,531 A 2/1996 Post et al.
5,514,117 A 5/1996 Lynn
5,515,871 A 5/1996 Bittner et al.
5,536,259 A 7/1996 Utterberg
5,575,780 A 11/1996 Saito
5,593,028 A 1/1997 Haber et al.
5,613,954 A 3/1997 Nelson et al.
5,632,735 A 5/1997 Wyatt et al.
5,647,845 A 7/1997 Haber et al.
5,685,866 A 11/1997 Lopez
5,752,942 A 5/1998 Doyle et al.
5,766,147 A 6/1998 Sancoff et al.
5,766,211 A 6/1998 Wood et al.
5,782,872 A 7/1998 Muller
5,795,336 A 8/1998 Romano et al.
5,817,083 A 10/1998 Shemesh et al.
5,820,609 A 10/1998 Saito
5,827,262 A * 10/1998 Neftel et al. .................. 604/414
5,837,262 A 11/1998 Golubev et al.
5,875,931 A 3/1999 Py
5,879,345 A 3/1999 Aneas
5,897,526 A 4/1999 Vaillancourt
5,934,510 A 8/1999 Anderson
5,984,899 A 11/1999 D'Alessio et al.
6,063,068 A 5/2000 Fowles et al.
D427,308 S 6/2000 Zinger
6,070,623 A 6/2000 Aneas
6,071,270 A 6/2000 Fowles et al.
6,090,091 A 7/2000 Fowles et al.
6,113,068 A 9/2000 Ryan
6,113,583 A 9/2000 Fowles et al.
6,142,446 A 11/2000 Leinsing
6,146,362 A 11/2000 Turnbull et al.
6,209,738 B1 * 4/2001 Jansen et al. .................. 141/329
6,221,065 B1 4/2001 Davis
6,245,056 B1 6/2001 Walker et al.
D445,501 S 7/2001 Niedospial, Jr.
6,253,804 B1 7/2001 Safabash
6,258,078 B1 * 7/2001 Thilly ........................... 604/411
6,387,074 B1 5/2002 Horppu et al.
6,453,956 B2 9/2002 Safabash
6,471,674 B1 10/2002 Emig et al.
6,517,523 B1 2/2003 Kaneko et al.
6,537,263 B1 * 3/2003 Aneas ........................... 604/411
6,571,837 B2 6/2003 Jansen et al.
6,591,876 B2 * 7/2003 Safabash ....................... 141/329
6,644,367 B1 11/2003 Savage et al.
6,685,692 B2 2/2004 Fathallah
6,715,520 B2 4/2004 Andreasson et al.
6,761,286 B2 7/2004 Py et al.
D495,416 S 8/2004 Dimeo et al.
6,786,244 B1 9/2004 Jones
D506,256 S 6/2005 Miyoshi et al.
7,000,806 B2 2/2006 Py et al.
7,080,672 B2 * 7/2006 Fournie et al. ................ 141/329
7,297,140 B2 * 11/2007 Orlu et al. ..................... 604/411
D570,477 S 6/2008 Gallogly et al.
D572,820 S 7/2008 Gallogly et al.
D577,438 S 9/2008 Gallogly et al.
D577,822 S 9/2008 Gallogly et al.
D582,033 S 12/2008 Baxter et al.
D605,755 S 12/2009 Baxter et al.
7,703,486 B2 * 4/2010 Costanzo ...................... 141/329
D616,984 S 6/2010 Gilboa
7,744,581 B2 6/2010 Wallen et al.
2001/0021825 A1 9/2001 Becker et al.
2001/0025671 A1 10/2001 Safabash
2002/0002352 A1 1/2002 Becker et al.
2002/0082586 A1 6/2002 Finley et al.
2002/0127150 A1 9/2002 Sasso
2002/0177819 A1 11/2002 Barker et al.
2003/0010717 A1 1/2003 Brugger et al.
2003/0070726 A1 * 4/2003 Andreasson et al. ......... 141/329
2003/0106610 A1 6/2003 Roos et al.
2003/0107628 A1 6/2003 Fowles et al.
2003/0199846 A1 10/2003 Fowles et al.
2003/0233083 A1 12/2003 Houwaert et al.
2004/0116858 A1 6/2004 Heinz et al.
2004/0199139 A1 10/2004 Fowles et al.
2004/0215147 A1 10/2004 Wessman et al.
2005/0215977 A1 9/2005 Uschold
2006/0025747 A1 2/2006 Sullivan et al.
2006/0106360 A1 5/2006 Wong
2006/0111667 A1 5/2006 Matsuura et al.
2006/0157984 A1 7/2006 Rome et al.
2006/0186045 A1 * 8/2006 Jensen et al. .................. 210/645
2007/0021725 A1 1/2007 Villette
2007/0060841 A1 3/2007 Henshaw
2007/0088313 A1 4/2007 Zinger et al.

| | | | | |
|---|---|---|---|---|
| 2007/0106244 | A1 | 5/2007 | Mosler et al. | |
| 2007/0179441 | A1 | 8/2007 | Chevallier | |
| 2007/0270759 | A1 | 11/2007 | Pessin | |
| 2007/0270778 | A9 | 11/2007 | Zinger et al. | |
| 2008/0045919 | A1 | 2/2008 | Jakob et al. | |
| 2008/0103453 | A1 | 5/2008 | Liversidge | |
| 2008/0103485 | A1 | 5/2008 | Kruger | |
| 2008/0172039 | A1 | 7/2008 | Raines | |
| 2008/0223484 | A1 * | 9/2008 | Horppu | 141/329 |
| 2008/0287920 | A1 | 11/2008 | Fangrow et al. | |
| 2008/0312634 | A1 | 12/2008 | Helmerson et al. | |
| 2009/0254042 | A1 | 10/2009 | Gratwohl et al. | |
| 2010/0137827 | A1 | 6/2010 | Warren et al. | |
| 2010/0204671 | A1 | 8/2010 | Kraushaar et al. | |
| 2010/0243099 | A1 | 9/2010 | Yodfat | |

FOREIGN PATENT DOCUMENTS

| | | | |
|---|---|---|---|
| DE | 2005519 | | 10/1979 |
| EP | 0255025 | | 2/1988 |
| EP | 0259582 | | 3/1988 |
| EP | 0285424 | | 10/1988 |
| EP | 0311787 | | 4/1989 |
| EP | 0376629 | | 7/1990 |
| EP | 0803267 | | 10/1997 |
| EP | 0819442 | | 1/1998 |
| EP | 0995453 | | 4/2000 |
| EP | 1060730 | | 12/2000 |
| EP | 1484073 | | 12/2004 |
| EP | 1731128 | A1 | 12/2006 |
| FR | 2757405 | | 6/1998 |
| FR | 2780878 | | 1/2000 |
| GB | 1579065 | | 11/1980 |
| JP | 49-12690 | | 5/1972 |
| JP | 288664 | | 7/1990 |
| JP | 3030963 | | 8/1996 |
| JP | 2000167022 | | 6/2000 |
| JP | 2001505092 | | 4/2001 |
| JP | 2001293085 | | 10/2001 |
| TW | 482670 | | 4/2002 |
| WO | WO 84/04672 | | 12/1984 |
| WO | WO 84/04673 | | 12/1984 |
| WO | WO 90/03536 | | 4/1990 |
| WO | WO 98/19724 | | 5/1998 |
| WO | WO 99/27886 | | 6/1999 |
| WO | WO 99/62578 | | 12/1999 |
| WO | WO0015292 | A2 | 3/2000 |
| WO | WO 00/35517 | | 6/2000 |
| WO | WO 01/80928 | | 11/2001 |
| WO | WO 02/02048 | | 1/2002 |
| WO | WO 02/11794 | | 2/2002 |
| WO | WO 02/064077 | | 8/2002 |
| WO | WO 02/076540 | | 10/2002 |
| WO | WO 2005/074860 | | 8/2005 |
| WO | WO 2006/082350 | | 8/2006 |
| WO | WO 2006/083333 | | 8/2006 |
| WO | WO 2008/115102 | | 9/2008 |
| WO | WO 2006/138184 | | 12/2009 |

OTHER PUBLICATIONS

Japan Application No. 2003-583539, Official Action dated May 1, 2009 (3 pages).

Japan Application No. 2003-577789, Official Action dated Feb. 24, 2009 (4 pages).

International Search Report, PCT/EP2008/067535 dated Oct. 13, 2009 (3 pages).

International Search Report, PCT/EP2008/067522 dated Aug. 12, 2009. (2 pages).

* cited by examiner

FLUID TRANSFER DEVICE

TECHNICAL FIELD

The present invention relates to a fluid transfer device and more specifically a piercing member protection device arranged with a first and a second fluid container.

BACKGROUND

A serious problem in connection with drug preparation, drug administration and other similar handling is the risk that medical and pharmacological staff are exposed to drugs or solvents which might escape into the ambient air. Medical and pharmacological staff are also frequently exposed to needles, syringes and piercing members in their daily work. Such exposure may lead to accidents such as the staff piercing or scratching themselves. This problem is particularly serious when cytotoxins, antiviral drugs, antibiotics and radiopharmaceuticals are concerned. Other hazardous areas may be sampling taking such as samples concerning virus infections or the like.

For this reason, there has been a need of safer systems for handling and administrating drugs and other medical substances.

Accordingly, U.S. Pat. No. 4,564,054 (Gustavsson) discloses a fluid transfer device for transferring a substance from one vessel to another vessel while avoiding leakage of liquid and gas contaminants by protecting the piercing member. The disclosed device comprises a first member designed as a hollow sleeve and having a piercing member provided with a passageway. The piercing member is attached to the first member which has a first barrier member at one end just opposite the tip of the piercing member. Thereby, the piercing member can be passed and retracted through the first barrier member which seals one end of the first member. The fluid transfer device further comprises a second member which is attached to or attachable to one of the vessels or to means arranged to communicate therewith. The second member has a second barrier member, and mating connection means arranged on the first and second members for providing a releasable locking of the members with respect to each other. The barrier members are liquid and gas-proof sealing members which seal tightly after penetration and retraction of the piercing member and prevent leakage of liquid as well as gas contaminants. In the connected position of the first and second members, the barrier members are located in such a way with respect to each other that the piercing member can be passed therethrough.

When performing infusion, it is often necessary to inject a drug or other medical substance into the infusion fluid inside an infusion bag or other infusion fluid container. This is often done by means of penetrating a septum or other fluid barrier of an injection port on the infusion bag or on the infusion fluid line with a needle of a syringe filled with the medical fluid in question. However, even before this it may be necessary to transfer the medical fluid from a vial to a syringe and then from the syringe to a secondary container.

In order to transfer a fluid, a first and a second fluid container is connected to a fluid transfer device. Such first and second fluid containers may be e.g., a vial and a syringe. In special cases the fluid transfer device may be in the form of a piercing member protection device to protect a piercing member. However, it has been found that some transfer devices lock the fluid containers with respect to each other in a non favourable position after assembly. Such a position may result in difficulties in e.g., reading the volume indication on at least one of the fluid containers. In attempts to eliminate this unfavourable position by e.g., turning the whole fluid transfer device it has surprisingly been found that such attempts cause an additional hazardous step for users e.g., medical staff when transferring hazardous fluids. If a syringe, vial or infusion system or the like is attached, the user's glove may e.g., be caught in the transfer device during turning of the syringe. Usually complications like this may lead to the gloves being torn. This may in turn lead to exposure to contaminants for the user. Further, contaminants may escape from the transfer device during the turning of the syringe. Even worse the connection means may be detached during such turning. In this worst case scenario, the piercing member is usually in its unsecured position and the user is very likely to be exposed to the sharp tip of the piercing member and the hazardous fluid. A further disadvantage is that one fluid container can be accidentally disconnected during use. A disconnection during use may expose not only a piercing member to a user but also expose the user to the hazardous fluid.

SUMMARY

It is therefore an object of the present invention to provide a fluid transfer device such as a piercing member protection device which partly or fully reduces the risk of complications during turning of the device or parts attached thereto. The present invention at least partly solves this problem by providing a fluid transfer device such as a piercing member protection device for transferring fluid from a first fluid container to a second fluid container. The fluid transfer device comprises a longitudinal axis A, a first connection part comprising connection means for connecting to the first fluid container. The fluid transfer device further comprises a second connection part rotatably mounted to said first connection part. The second connection part further comprises connection means for connecting the second fluid container. The present invention allows any fluid container attached to the fluid transfer device to be turned easily and safely without complications.

The fluid transfer device may further be arranged with a first locking means, wherein the first locking means substantially prevents the first connection part from turning in a predetermined direction with respect to the second connection part while still allowing it turn in a direction opposite of the predetermined direction. The mentioned embodiment has several advantages. One advantage is that the fluid transfer device may be attached to a first fluid container by a turning motion (in the predetermined direction) without using the turning function between the first and second connection part. This will also have the advantage of preventing the fluid transfer device from being unscrewed after attachment with the first fluid container since any turning in the direction opposite of the predetermined direction will only result in the turning between the first and second connection part of the fluid transfer device due to the first locking means.

In one embodiment, the fluid transfer device is a piercing member protection device. The piercing member protection device may comprise a piercing member protection part having a protection chamber to protect a piercing member. The piercing member protection device has a secured position, in which at least the tip of said piercing member is enclosed within the protection chamber of the piercing member protection part, so as to prevent the tip of the piercing member from exposure. The piercing member protection device further has an unsecured position, in which the tip of the piercing member is arranged outside the protection chamber of said piercing member protection part. The first locking means on the fluid transfer device can enable at least a 90° turn, e.g., at least a 180° turn, at least a 270° turn, or at least a 360° turn of the second connection part. The latter first locking means has the advantage of letting an attached second fluid container be turned fully around, giving the user full access to any indications present on the surface of the second fluid container. In one embodiment of the present invention the first locking means connects the first and second connection parts by means of a locking groove and a locking protrusion, such a locking groove is arranged transversally to the longitudinal axis A around the periphery of the first connection part while the locking protrusion is arranged on the second connection part. In an alternative embodiment of the present invention the locking protrusion may be arranged on the second connection part of the fluid transfer device while the locking groove is arranged on the first connection part. In the cases when at least a 90°, 180° or a 270° turn of the fluid transfer device is preferable, the first locking means connects to the first and second connection part by means of a locking groove arranged transversally to the longitudinal axis A around at least a part of the periphery of the connection part.

The locking protrusion may by in the form of a saw tooth element, i.e. a ratchet, which interacts with the locking groove. There can be between 1 to 30 saw tooth elements, e.g., 2 to 10, or 2 to 5 saw tooth elements. The saw tooth elements can be arranged at an angle between 2 to 15°, e.g., 4 to 12°, or 5 to 10° with respect to an axis perpendicular to the longitudinal axis A. Such angle allows for a smooth turning in one direction while still enabling an efficient prevention of turning in the predetermined direction.

In one embodiment of the present invention, the fluid transfer device is equipped with the mentioned piercing member in order to transfer fluid from one fluid container to a second fluid container. This embodiment of the present invention is advantageous because it reduces the amount of occasions in which a user may be exposed to a piercing member. The piercing member might however be arranged on one of the fluid containers which is arranged for connection with the fluid transfer device in order to transfer fluid from the first fluid container to the second fluid container. The fluid transfer device may further comprise a stabilization member arranged to stabilize or guide the piercing member. Stabilization of the piercing member, regardless of whether it is arranged on the second connection part or an attachable fluid container, is important to prevent the piercing member from breaking or bending. Such a stabilization member can comprise a hollow tube arranged substantially along the longitudinal axis A or parallel thereto, wherein the hollow tube is arranged to at least partly enclose the piercing member. In cases were the piercing member is arranged on a fluid container the stabilization member at least partly enclose the piercing member after assembly.

The fluid transfer device may optionally be used in various different fields of technology such as food manufacturing technology or medical technology. In the embodiments when the fluid transfer device is a piercing member protection device or a fluid transfer connector, it can be a medical piercing member protection device or medical fluid transfer connector, for example.

DEFINITIONS

With the term "piercing member" it is meant a substantially hollow object, such as a needle like tube or a needle, which may pierce a membrane or similar in order to withdraw or infuse a gas fluid, a liquid fluid or a mixture thereof (i.e. a fluid). The mentioned membrane may be the skin of a patient or a flexible barrier member on e.g., a vial or on an infusion bag or the like.

With the term "medical" piercing member protection device or "medical" fluid transfer device is meant a device which is used directly or indirectly in the medical field of technology e.g., in hospital environments or hospital like environments, pharmaceutical industry, home care etc. Examples of medical devices are needles, needle like tubes, syringes, infusion bags, medical fluid transfer devices, medical vials, medical fluid containers, medical sampling containers or the like.

With the term "interacting protrusion element" is meant at least one element which interacts with at least one part of the first locking means when said first locking means is in the form of a locking protrusion or a saw tooth arrangement as described. Although a saw tooth may interact with a protrusion, it can likewise interact with a groove. The "interacting protrusion element" is then considered to be the material which fully or partly defines that groove (e.g., the wall of the groove).

DETAILED DESCRIPTION

Generally dependent upon how the first and the second connection part are arranged to interact via the first locking means and the mounting means, the fluid transfer device may display the following functions:

1) The first locking means may be arranged so as to prevent the turning of the first connection part with respect to the second connection part in a predetermined direction. In this embodiment the first locking means is always engaged, no play exists between the first and the second connection part. As an example, a saw tooth protrusion and an interacting protrusion element will always be engaged.

2) The first locking means may be arranged so as to prevent the turning of the first connection part with respect to the second connection part in a predetermined direction and one position in which the first connection part may be turned in any direction with respect to the second connection part. This embodiment has a play between the first connection part and the second connection part so that e.g., a saw tooth protrusion and an interacting protrusion element will be able to disengage.

3) The first locking means may be arranged so as to prevent the turning of the first connection part with respect to the second connection part in a predetermined direction during assembly with a fluid container and one position in which the first connection part may, after assembly, be turned in any direction with respect to the second connection part and whereby the first locking means can not again be engaged after disengagement. This embodiment, which actually is another embodiment of the embodiment listed under point 2, can be achieved by suitably adapt the size of the play with respect to the length of the second connection part and the mounting means.

Figure 1:
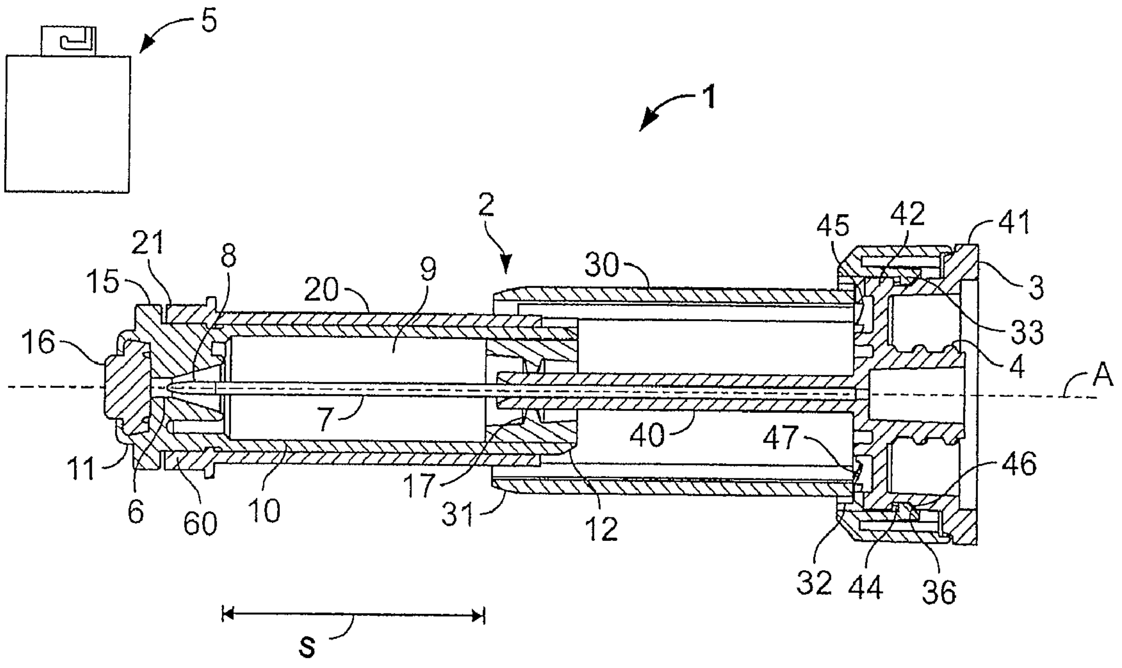
FIG. 1 shows a cross section of a fluid transfer device in the form of a piercing member protection device according to the present invention illustrated in its secured position.

These embodiments will be further described in greater detail with the aid of the following examples:

In FIG. 1 a fluid transfer device according to the present invention in the form of a piercing member protection device 1 is illustrated having a first connection part 2 in the form of a piercing member protection part 2 which is rotatably mounted to a second connection part 3. The piercing member protection part 2 is in FIG. 1 shown in its secured position.

The piercing member protection device 1 comprises a longitudinal axis A. The piercing member protection part 2 comprises a first member 10, a second member 20 and a third member 30. The first member 10 has a first end 11 and a second end 12, the first end 11 comprises connection means 15 for connecting to a first container 5. The second member 20 at least partly encloses the first member 10 and the third member 30 at least partly encloses the first 10 and the second member 20. The third member 30 has a first end 31 and a second end 32. The second end 32 of the third member 30 comprises means for attaching the third member to the second connection part 3.

The first end 11 of the first member 10 also comprises an injection port 6 through which at least a part of a piercing member 7 is to be guided through to the first container 5 when connected thereto, i.e. when the piercing member protection device goes from the secured position to the unsecured position. When the piercing member protection part 2 is in the secured position, at least the tip 8 of the piercing member 7 is fully enclosed inside the first member 10 so as to prevent the sharp tip 8 of the piercing member 7 coming in contact with a user. In this embodiment of the present invention the first member 10 defines a protection chamber for the tip of the piercing member 7. The piercing member 7 may either be attached, as described below to the fluid transfer device, or to a separate device, such as a fluid container, which can be attached to the fluid transfer device 3.

The first, second and third members 10, 20, 30 can be manufactured from any suitable material, but they preferably comprise a thermoplastic material such as polypropylene, polyethylene, polyurethane, polystyrene, polyoxymethylene, acrylonitrile-butadienestyrene copolymer (ABS), polyethylene terephthalate or mixtures thereof. The first, second and third members 10, 20, 30 can be made of different materials or of the same material. In one embodiment, the first member 10 is made of a transparent material in order to allow the user of the device to easily see if proper function is achieved. A suitable material should be somewhat flexible to allow for the second member 20 to be threaded onto the first member 10 without major difficulties but rigid enough to provide enough protection for the piercing member arranged inside the first member 10 when such is present.

Figure 2:
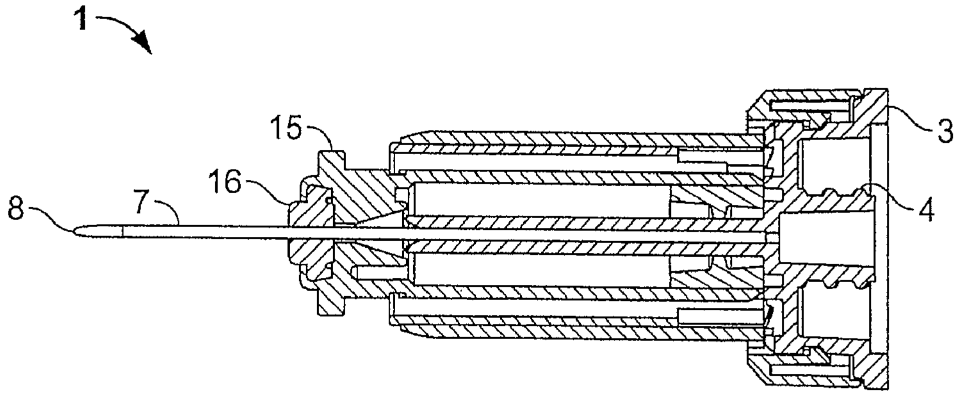
FIG. 2 shows a cross section of the fluid transfer device according to the present invention in FIG. 1 as seen from a slightly different angle. The piercing member protection device is in its unsecured position.

The third member 30 may slide along the longitudinal axis A from a secured position (as shown in FIG. 1) to an unsecured position (as shown in FIG. 2). It is noted that an unsecured position is achieved somewhere along the longitudinal axis A dependent on the length of the piercing member 7. In some embodiments, the third member 30 can be moved a minimum length of 10% of the total length (i.e. the total length being the maximum length possible to move the third member 30) before the fluid transfer device is in its unsecured position. The total length is illustrated in FIG. 1 with a slide arrow S. The third member 30 may further be turned with respect to the second member 20 from a locked position to an unlocked position. When the piercing member protection device is in its unsecured position, a fluid communication typically is provided between the first and the second container, while in its secured position, no fluid communication is provided between the first and the second container. The main difference is however that in its unsecured position the tip 8 of the piercing member is exposed outside the protection chamber 9 of the first member 10 exposing the tip 8 to any user operating the fluid transfer device.

Engagement means 60 are arranged on the first end 21 of the second member 20 to engage a first container 5 (shown schematically in FIG. 1) to prevent the second member 20 from turning during connection.

An example of a first container 5 and its connection means is described in greater detail in WO 03/030809 A1. The engagement means 60 are in the form of a longitudinal protrusion extending in the direction of the longitudinal axis A which engages the first container 5 in a corresponding groove on the first container. It is however well within the boundaries of the present invention that the engagement means 60 may be constituted by a groove on the second member 20 which engages a corresponding protrusion on the first container 5. As an alternative the second member 20 may be held in place by the user during turning, in which case no engagement means are necessary.

The first end 11 of the first member 10 can be equipped with a flexible barrier member. It may further be designed and arranged for creating a double-membrane sealing when the connection means 15 is connected to the first container 5. In such case the first container may be e.g., an infusion bag of an infusion system, an infusion fluid line of the mentioned infusion system or a separate spike device exhibiting a flexible barrier member. In some embodiments, the first end 11 of the first member 10 is designed and arranged for all these cases. Double membrane bayonet couplings are known per se from the U.S. Pat. No. 4,564,054 for example and will hereafter not be described in greater detail. As a measure of safety a second flexible barrier member 17 may be provided at the second end 12 of the first member 10. The flexible barrier members 16, 17 are liquid and gas-proof sealing members which seal tightly around the piercing member to prevent leakage of liquid as well as gas contaminants. In cases where the piercing member is arranged on the second connection part 3, it can extend through the second flexible barrier member so its tip 8 is arranged inside protection chamber 9 of the first member 10.

As described the piercing member protection part 2 comprises of three members arranged together in working cooperation. It is however within the boundaries of the present invention that the piercing member protection part 2 may be designed in different ways.

As illustrated in FIG. 1 the second connection part 3 comprises a turning grip 41 intended to aid a user to get a firm grip of the second connection part 3 in order to securely turn the second connection part 3. The second connection part 3 has a mounting part 42 arranged to the turning grip 41 which after assembly is rotatably mounted to the first connection part 2, in this embodiment the third member 30. The mounting part 42 is at least partly arranged inside the third member 30. In this embodiment, the mounting part 42 comprises dual function locking means. A mounting means 44 prevents the second connection part 3 from sliding along the longitudinal axis A while at the same time allowing for a rotational movement, i.e. to be turned, of the second connection part 3 with respect first connection part 2, in this embodiment the piercing member protection part 2.

A first locking means 45 prevents the second connection part 3 from turning in a predetermined direction, which is either clock-wise or anti clock-wise, with respect to the first connection part 2. Connection means 4 for connection to a syringe or similar is arranged on the second connection part 3.

The second connection part 3 is mounted to the first connection part 2 by mounting means 44 comprising a locking groove 46 arranged transversally to the longitudinal axis A around the periphery of the mounting part 42. The locking groove interacts with at least one locking protrusion 33 arranged on the inside of the third member 30. Generally, the locking protrusion 33 can be slightly flexible so as to allow for an easy assembly of the third member 30 and the second connection part 3. When the locking protrusion 33 locks into the locking groove 46, and thereby the first connection part 2, it substantially locks the second connection part 3 from axial movement along the longitudinal axis A with respect to the first connection part 2, while at the same time, allowing for the second connection part 3 to be turned with respect to the first connection part 2.

It is to be understood that by substantially locking the second connection part 3 from axial movement along the longitudinal axis A with respect to the first connection part 2 does not necessarily mean a firm fixation of the second connection part 3 with respect to the first connection part 2. Instead the second connection part 3 may very well have a certain play with respect to the first connection part 2. Such play can allow the first connection part 2 to disengage with the second connection part 3 so that when the first locking means 45 are disengaged the first connection part 2 may be turned in any direction with respect to the second connections means 3. In this embodiment the first connection part 2 and the second connection part 3 has two positions, one in which the first locking means 45 is engaged so as to prevent the turning of the first connection part 2 with respect to the second connection part 3 in a predetermined direction and one position in which the first connection part 2 may be turned in any direction with respect to the second connection part 3.

Although the mounting means 44 has been described as a locking groove 46 it is within the boundaries of the present invention that any means which may provide the desired effect of locking the movement of the second connection part 3 along the longitudinal axis A while at the same time allowing the second connection part 3 to be turned in at least one direction with respect to the first connection part 2 may be suitable as mounting means 44.

In the illustrated embodiment in FIGS. 1-3, the first locking means 45 comprise a plurality of saw tooth protrusions 47 arranged on the mounting part 42. The first connection part 2, and more specifically in the shown embodiment of the present invention, the third member 30 on the piercing member protection device, comprises an interacting protrusion element such as an interacting saw tooth protrusion (not shown in FIG. 1) which after assembly with the second connection part 3 interacts with the plurality of saw tooth protrusions 47 on the second connection part 3 so that the second connection part is only able to turn in a clock-wise or an anti clock-wise direction after assembly. Although the first locking means 45 has been described as a saw tooth protrusion it is within the boundaries of the present invention that any means which may provide the desired effect of preventing the second connection part 3 from turning in one direction (e.g., in a clock-wise direction) while allowing for the second connection part 3 to be turned in an opposite direction (e.g., anti clock-wise direction) may be suitable as second locking means 45.

The mounting means 44 and the first locking means 45 are in the shown embodiment in FIG. 1 illustrated as separate means. It is within the boundaries of the present invention that the mounting means 44 and the first locking means 45 are integrally formed.

The second connection part 3 further comprises a stabilization member 40 arranged to stabilize the piercing member 7. The stabilization member 40 extends through the third member 30 into the confined chamber defined by the first member 10 and the first and second flexible membrane barriers 16, 17 of the first member 10. The stabilization member 40 can be is formed of a hollow tube which at least partly encloses the piercing member in order to prevent the piercing member from breaking or bending. The second connection part 3 is further equipped with connection means 4 for connection to a second fluid container.

In one embodiment of the present invention the stabilization member 40 may be arranged with said mounting means 44. When the stabilization member is in the form of a hollow tube, the hollow tube comprises an outer surface and a protrusion extending away from the longitudinal axis A on the outer surface of the hollow tube. In this case the protrusion can have an inclining surface so as to enable a simple connection to said first connection part 2.

In FIG. 2 the fluid transferring device 1 is shown in its unsecured position, i.e. the tip 8 of the piercing member 7 is exposed to the environment. The piercing member 7 has pierced the flexible barrier member 16 in order to provide for a fluid communication between a first fluid container e.g., an infusion bag or a vial (attached to connection means 15 of the first member 10) and a second fluid container e.g., a syringe (attached to connection means 4 of the second connection part 3). When a fluid transfer device 1 as shown in FIGS. 1 and 2 is in its secured or unsecured position it is important to allow the second fluid container to be turned in order to easily see a volume indication or similar on the second container. The second connection part 3 enables this even in the unsecured position as shown in FIG. 2.

Figure 3A:
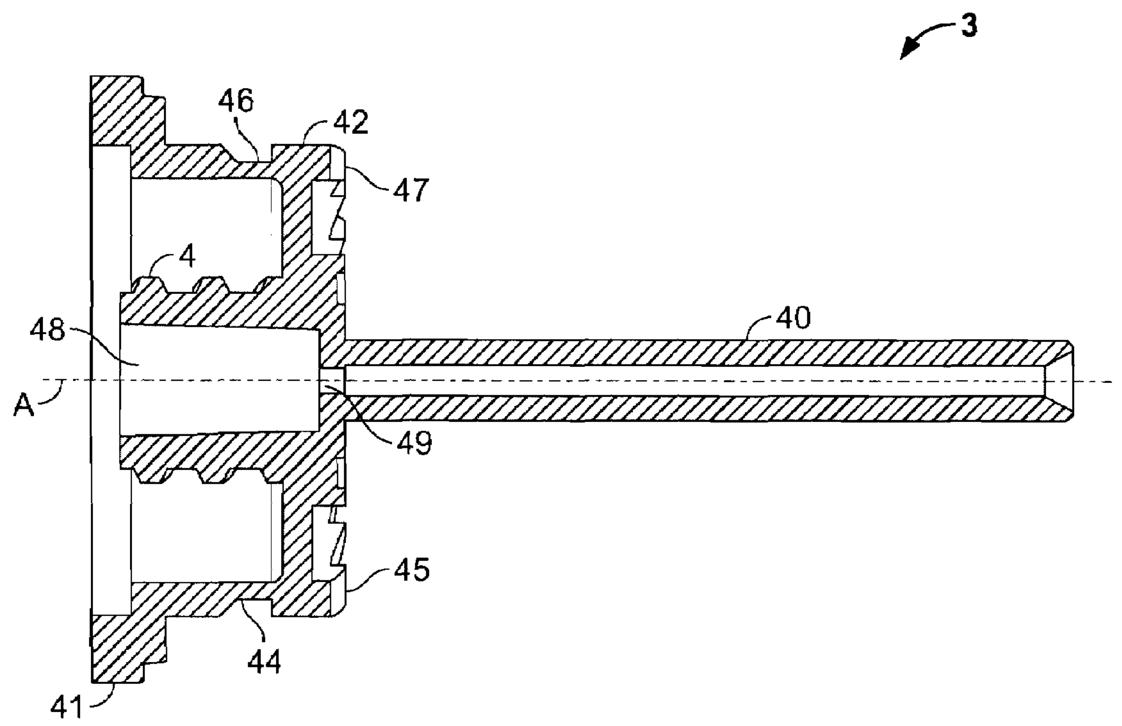
FIG. 3*a* shows a cross section of a fluid transfer device according to the present invention.

FIG. 3*a* shows a cross section of a second connection part 3 of the fluid transfer device according to the present invention. As mentioned, the second connection part 3 is equipped with connection means 4 for connection to a syringe or similar. The connection means 4 comprises a threaded coupling onto which e.g., a syringe may be screwed in order to provide a fluid flow through the second connection part 3 and a first connection part 2 when such is mounted. When screwing the second fluid container onto the threaded coupling the first locking means 45 engages the first connection part 2 (if there is a play) so as to lock the second connection part 3 from turning in a predetermined direction, i.e. the direction of which the second fluid container is screwed. Likewise after the second fluid container has been screwed onto the threaded coupling the second fluid container cannot (without much effort or actively prevention of the second connection part 3 from turning) be unscrewed because the first locking means 45 allows the second fluid container and the second connection part 3 to be turned in a direction opposite to the predetermined direction.

The second connection part 3 can be equipped with a stabilization member 40 arranged to stabilize a piercing member when such is arranged in the second connection part 3. The connection means 4 further defines an opening 48 into which a part of e.g., a syringe may be screwed. A fluid channel orifice 49 is arranged to provide for a fluid channel between the opening 48 and the piercing member 7. If no piercing member is arranged on the second connection part 3, a flexible barrier member (not shown) is advantageously arranged to cover the fluid channel orifice 49 in order to facilitate a safe environment for the user.

The second connection part 3 comprises a turning grip 41 intended to aid a user to get a firm grip of the second connection part 3 to securely turn the second connection part 3. Such a turning grip 41 is however not necessary as the second connection part 3 may be turned by means of the second fluid container after attachment with the second connection part 3. However, the turning grip 41 may advantageously be used to hold the second connection part 3 in a firm grip during disengagement with a second fluid container.

As described earlier a mounting part 42 is arranged to the turning grip 41, the mounting part 42 connects and holds the piercing member protection part after assembly. The mounting part 42 connects to the piercing member protection part by means of mounting means 44, illustrated in FIG. 1 as a locking groove 46 arranged transversally to the longitudinal axis A around the periphery of the mounting part 42. The mounting part 42 is during assembly with a piercing member protection part of a fluid transfer device attached with at least one interacting locking protrusion 33 of the mentioned piercing member protection part (see FIGS. 1 and 2).

A first locking means 45 is arranged on the mounting part 42. The first locking means 45 is in FIG. 3*a*. illustrated as a plurality of saw tooth protrusions 47 which are arranged in a circle around the stabilization member 40. The plurality of saw tooth protrusions 47 interacts with interacting means on the first connection part 2, in the illustrated embodiment the piercing member protection part, so as to allow for a 360° turn of the second connection part in a predetermined direction. The interacting means may as mentioned be interacting saw tooth elements, however, any kind of means able to interact with a saw tooth protrusions 47 in order to allow for a 360° turn of the second connection part 2 in a predetermined direction may be used. The first locking means 45 can be designed for a clock-wise turn or an anti clock-wise turn of the second connection part 3, its however within the boundaries of one embodiment of the present invention that the first locking means 45 allows for a step-wise turning in both a clock-wise and/or an anti clock-wise direction of the second connection part 3. Such step-wise turning is advantageous since it induces a moment of inertia to the second connection part 3 which prevents a connected syringe or similar from turning too easily. The first locking means 45 has in such an embodiment of the present invention a plurality of e.g., sinusoidal shaped protrusions (wave like) more than saw tooth shaped protrusions as described earlier. Of course the piercing member protection part is equipped with corresponding means in order to facilitate such controlled turning of the second connection part.

Figure 3B:
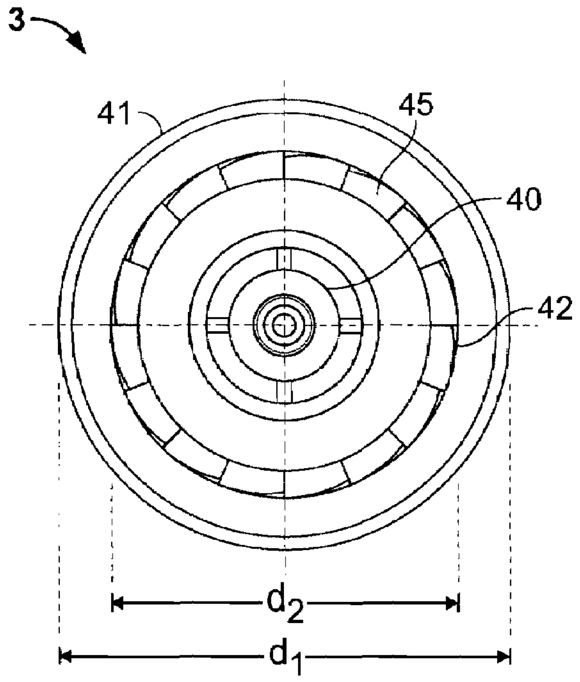
FIG. 3*b* shows a front view of a fluid transfer device according to the present invention.
Figure 3C:
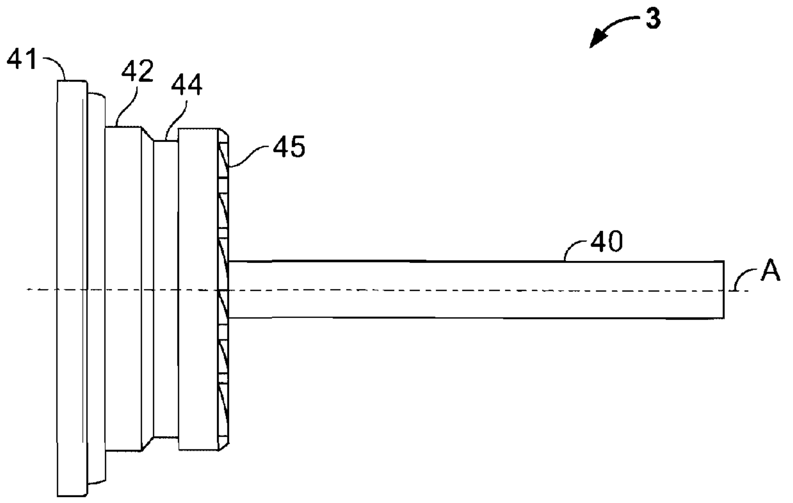
FIG. 3*c* shows a side view of a fluid transfer device according to the present invention.

FIG. 3*b* shows the second connection part 3 as seen along the longitudinal axis A. The first locking means 45 circles the stabilization means 40 in order to provide for a 360° turn of the second connection part. The second connection part 3 has in the shown embodiment of the present invention a circular cross section. The turning grip has a diameter $d_1$ while the mounting part 42 has a diameter $d_2$. In the shown embodiment of FIG. 3*b* $d_2$ is smaller than the inner diameter of the third member 30 in order to facilitate the assembly of the second connection part 3 into the third member 30 of first connection part 2 of the fluid transfer device 1 as described earlier. This is further illustrated in FIG. 3*c* in which a side view of the second connection part of the present invention is shown. Further are a mounting means 44 and a first locking means 45 arranged on the mounting part 42 which in turn is arranged to a turning grip 41. Stabilization means 40 extends along the longitudinal axis A out from the centre of the connection means 42. In the shown embodiment of the present invention the turning grip 41, the connection means 42 and the stabilization means 40 are formed in one piece of material, it is however within the boundaries of the present invention that the turning grip 41, the mounting means 42 and the stabilization means 40 are formed of separate pieces of material attached to each other.

In one embodiment, the first member of the piercing member protection device can have a cylindrical inside. For example, to simplify manufacturing, the first member of the piercing member protection device can be a cylinder member. Likewise, the second and third members can be cylinder members.

Figure 4:
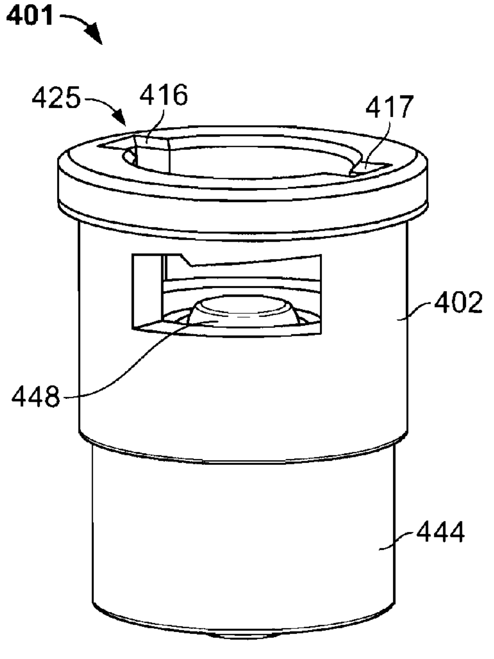
FIG. 4 shows a fluid transfer device according to the present invention as seen in perspective.

FIG. 4 shows a fluid transfer device 401 according to an embodiment of the present invention. The fluid transfer device 501 has connection means 415 having a neck element comprising two guiding members 416, 417 to which a first fluid container, such as an injector, may be connected. The first connection part 402 is seen provided with mounting means 444 which by the second connection part is mounted by to the first connection means 402. A barrier member 448 can be seen through the neck element of the connection means 415.

Figure 5:
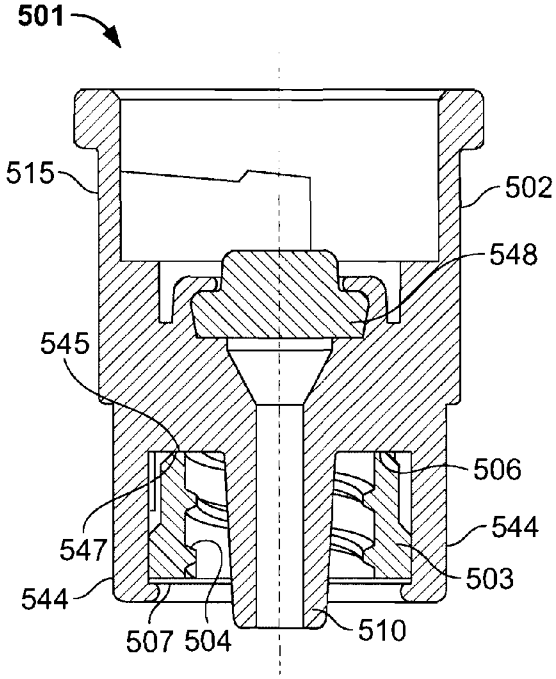
FIG. 5 shows a cross section of the fluid transfer device in FIG. 4.

FIG. 5 is a cross section of the embodiment shown in FIG. 4 of the present invention. FIG. 5 shows the cross section of a fluid transfer device 501 according to the present invention in the form of a connector having a first connection part 502 with a cylinder like form which is rotatably mounted to a second connection part 503 via mounting means 544. The mounting means 544 substantially prevents the second connection part 503 from sliding along the longitudinal axis A while at the same time allowing for a rotational movement, i.e. to be turned, of the second connection part 503 with respect to the first connection part 502. In the shown embodiment mounting means 544 comprises a cylinder shaped extension of the first connection part 502 which at least partly encloses the second connection part 503. However it does not enclose the second connection part 503 so as to occlude the connection means 504. As seen in FIG. 5 the first connection part 502 comprises connection means 515 to connect to a first fluid container, e.g., an injector as described in WO 2004/004806 (injection component 29).

A first locking means 545, as described in earlier embodiments, prevents the second connection part 503 from turning in a predetermined direction, which is either clock-wise or anti clock-wise, with respect to the first connection part 502. As in the earlier embodiments the first locking means 545 may comprise a plurality of saw tooth protrusions which are arranged in a circle on the second connection part 503. The plurality of saw tooth protrusions interacts with interacting means on the first connection part 502, so as to allow for at least a 90°, e.g., at least a 180°, at least a 270°, or at least a 360° turn of the second connection part in a predetermined direction.

Connection means 504, in the form of a threaded coupling, in some embodiments forming part of a luer-lock coupling, for connection to an infusion bag or similar is arranged on the second connection part 503. In the depicted embodiment, the second connection part 503 has substantially the shape of a rotatable cylinder having a threaded coupling arranged on the inside of the cylinder (i.e. the inner surface) while having a smooth surface on the outer surface of the cylinder. The second connection part 503 has a first and a second end 506, 507. The first end 506 is arranged towards the first connection part 502 while the second end 507 of the second connection part 503 is arranged facing away from the first connection part 502. The second connection part 503 is encircling a conical shaped protrusion 510 extending out from the first connection part 502, the conical shaped protrusion 510 forms together with the threaded coupling part of a luer-lock coupling.

The second connection part 503 may have a play with respect to the first connection part 502. Such play can allow the first connection part 502 to partly disengage with the second connection part 503 so that the first locking means 545 is disabled. The first connection part 502 may then be turned in any direction with respect to the second connections means 503. In this embodiment the first connection part 502 and the second connection part 503 have two positions, one in which the first locking means 545 is engaged so as to prevent the turning of the first connection part 502 with respect to the second connection part 503 in a predetermined direction and one position in which the first connection part 502 may be turned in any direction with respect to the second connection part 503.

If as shown in FIG. 5, the second connection part 503 comprises of an open ended cylinder, i.e. the first end 506 of the second connection part 503 is open towards the first connection part 502, and the mounting means 544 typically is made 3-15% longer than the second connection part 503. The second connection part 503 will when threaded onto a fluid container be unable to engage the first locking means 545 again after disengagement of the first locking means 545. This is due to that the fluid container is allowed to maintain the play since it will run through the second connection part 503 and displace the second connection part 503 towards to first connection part 502. In this sense, a permanent disengagement of the first locking means is achieved. Once the first locking means 545 is disengaged it can not again engage since no matter how the second connection means 503 is turned the first locking means 545 will not engage again.

In the illustrated embodiment in FIG. 5, the first locking means 545 comprise a plurality of saw tooth protrusions 547 (as described earlier in FIG. 1-3). The first connection part 502 comprises an interacting protrusion element such as an interacting saw tooth protrusion (not shown in FIG. 5) which after assembly with the second connection part 503 interacts with the plurality of saw tooth protrusions 547 on the first end 506 of the second connection part 503 so that the second connection part is only able to turn in a clock-wise or an anti clock-wise direction after engagement. Although the first locking means 545 has been described as a protrusion such as a saw tooth protrusion, and interacting protrusion element, it is within the boundaries of the present invention that any means which may provide the desired effect of preventing the first connection part 502 from turning in a predetermined direction (e.g., in a clock-wise direction) with respect to the second connection part 503 may be suitable as first locking means 545 while still allowing it to turn in a direction opposite of the predetermined direction.

The mounting means 544 and the first locking means 545 are in the shown embodiment in FIG. 1-5 illustrated as separate means. It is within the boundaries of the present invention that the mounting means 544 and the first locking means 545 are integrally formed. The first locking means 545 may for instance be arranged on the mounting means 544.

A flexible barrier member 548 is arranged in the first connection part 502. The flexible barrier member 548 is a liquid and gas-proof sealing member which may seal tightly around a piercing member to prevent leakage of liquid as well as gas contaminants before as well as after insertion or retraction of the piercing member. A piercing member may be arranged either as described earlier to the fluid transfer device 501, or as a separate device, e.g., on a fluid container such as a syringe, which can be arranged to the fluid transfer device 501.

What is claimed is:

1. A piercing member protection device for transferring fluid from a first fluid container to a second fluid container, wherein said piercing member protection device comprises a piercing member, a longitudinal axis, and a first connection part comprising connection means for connecting to said first fluid container, wherein said piercing member protection device further comprises a second connection part rotatably mounted to said first connection part by a means for mounting that permits at least a 360 degree turn of said second connection part with respect to said first connection part and that prevents said second connection part from sliding along said longitudinal axis, wherein said second connection part comprises connection means for connecting to said second fluid container, and wherein said first connection part comprises a first member, a second member capable of at least partly enclosing said first member, and a third member capable of at least partly enclosing said second member.

2. A piercing member protection device according to claim 1, wherein said piercing member protection device is further arranged with a first locking means, wherein said first locking means substantially prevents said first connection part from turning in a predetermined direction with respect to said second connection part while still allowing said first connection part to turn in a direction opposite of said predetermined direction.

3. A piercing member protection device according to claim 2, wherein said first locking means comprises at least one protrusion, and wherein said at least one protrusion engages at least one interacting protrusion element on said first connection part.

4. A piercing member protection device according to claim 1, wherein said piercing member protection device comprises a piercing member protection part comprising a protection chamber adapted to protect said piercing member, said piercing member protection device having a secured position in which at least the tip of said piercing member is enclosed within said protection chamber of said piercing member protection part so as to prevent said tip of said piercing member from exposure, and an unsecured position in which said tip of the piercing member is arranged outside the protection chamber of said piercing member protection part.

5. A piercing member protection device according to claim 4, wherein said mounting means connects to said piercing member protection part by means of a locking groove arranged transversally to the longitudinal axis around the periphery of a mounting part.

6. A piercing member protection device according to claim 1, wherein said piercing member protection device further comprises a stabilization member arranged to stabilize said piercing member.

7. A piercing member protection device according to claim 6, wherein said stabilization member comprises a hollow tube arranged along the longitudinal axis or parallel thereto, wherein said hollow tube is arranged to at least partly enclose said piercing member.

8. A piercing member protection device according to claim 1, wherein said piercing member protection device is a medical piercing member protection device.

9. A piercing member protection device according claim 1, wherein the first connection part and the second connection part have two positions, one position in which a first locking means is engaged so as to prevent turning of the first connection part with respect to the second connection part in a predetermined direction, and one position in which the first connection part may be turned in any direction with respect to the second connection part.

10. A piercing member protection device according to claim 9, wherein said two positions are enabled by means of a play between the first connection part and the second connection part.

11. A piercing member protection device according to claim 1, wherein said connection means on said second connection part interacts with a first locking means so that a predetermined direction in which said first connection part is prevented from turning with respect to said second connection part is the same direction as said second connection part is turned in order to connect a second fluid container thereto.

12. A piercing member protection device according to claim 1, wherein said connection means on said first connection part interacts with a first locking means so that a predetermined direction in which said first connection part is prevented from turning with respect to said second connection part is the same direction as said second connection part is turned in order to connect a first fluid container thereto.

13. A piercing member protection device according claim 1, wherein said first connection part is provided with a barrier member.

14. A piercing member protection device for transferring fluid from a first fluid container to a second fluid container, wherein said piercing member protection device comprises a piercing member, a longitudinal axis, and a first connection part comprising connection means for connecting to said first fluid container, wherein said piercing member protection device further comprises a second connection part rotatably mounted to said first connection part by a means for mounting that permits at least a 360 degree turn of said second connection part with respect to said first connection part and that prevents said second connection part from sliding along said longitudinal axis, wherein said second connection part comprises connection means for connecting to said second fluid container, and wherein said piercing member protection device comprises a first locking means that substantially prevents said first connection part from turning in a predetermined direction with respect to said second connection part while still allowing said first connection part to turn in a direction opposite of said predetermined direction.

15. A piercing member protection device according to claim 14, wherein said piercing member protection device comprises a piercing member protection part comprising a protection chamber adapted to protect said piercing member, said piercing member protection device having a secured position in which at least the tip of said piercing member is enclosed within said protection chamber of said piercing member protection part so as to prevent said tip of said piercing member from exposure, and an unsecured position in which said tip of the piercing member is arranged outside the protection chamber of said piercing member protection part.

16. A piercing member protection device according to claim 15, wherein said mounting means connects to said piercing member protection part by means of a locking groove arranged transversally to the longitudinal axis around the periphery of a mounting part.

17. A piercing member protection device according to claim 14, wherein said piercing member protection device further comprises a stabilization member arranged to stabilize said piercing member.

18. A piercing member protection device according to claim 17, wherein said stabilization member comprises a hollow tube arranged along the longitudinal axis or parallel thereto, wherein said hollow tube is arranged to at least partly enclose said piercing member.

19. A piercing member protection device according to claim 14, wherein said first locking means comprises at least one protrusion, and wherein said at least one protrusion engages at least one interacting protrusion element on said first connection part.

20. A piercing member protection device according to claim 14, wherein said piercing member protection device is a medical piercing member protection device.

21. A piercing member protection device according claim 14, wherein the first connection part and the second connection part have two positions, one position in which a first locking means is engaged so as to prevent turning of the first connection part with respect to the second connection part in a predetermined direction, and one position in which the first connection part may be turned in any direction with respect to the second connection part.

22. A piercing member protection device according to claim 21, wherein said two positions are enabled by means of a play between the first connection part and the second connection part.

23. A piercing member protection device according to claim 14, wherein said connection means on said second connection part interacts with a first locking means so that a predetermined direction in which said first connection part is prevented from turning with respect to said second connection part is the same direction as said second connection part is turned in order to connect a second fluid container thereto.

24. A piercing member protection device according to claim 14, wherein said connection means on said first connection part interacts with a first locking means so that a predetermined direction in which said first connection part is prevented from turning with respect to said second connection part is the same direction as said second connection part is turned in order to connect a first fluid container thereto.

25. A piercing member protection device according claim 14, wherein said first connection part is provided with a barrier member.

* * * * *